(12) United States Patent
Walsh

(10) Patent No.: US 6,497,358 B1
(45) Date of Patent: Dec. 24, 2002

(54) RECORD AND VERIFICATION METHOD AND SYSTEM FOR RADIATION THERAPY

(76) Inventor: Christopher S. Walsh, 303 Falling Creek Rd., Fredericksburg, VA (US) 22401

(*) Notice: Subject to any disclaimer, the term of this patent is extended or adjusted under 35 U.S.C. 154(b) by 0 days.

(21) Appl. No.: 09/473,138

(22) Filed: Dec. 28, 1999

Related U.S. Application Data (60) Provisional application No. 60/153,243, filed on Sep. 13, 1999, provisional application No. 60/155,644, filed on Sep. 24, 1999, provisional application No. 60/155,800, filed on Sep. 27, 1999, provisional application No. 60/161,416, filed on Oct. 25, 1999, and provisional application No. 60/163,084, filed on Nov. 2, 1999.

(51) Int. Cl.⁷ .............................................. G06K 5/00
(52) U.S. Cl. .................. 235/380; 235/382; 235/383; 235/375; 705/64; 705/65; 705/67; 705/72; 705/75; 705/3
(58) Field of Search .......................... 239/380, 382, 239/383, 375; 705/64, 65, 67, 72, 75, 3

(56) References Cited

U.S. PATENT DOCUMENTS

| | | |
|---|---|---|
| 3,714,486 A | 1/1973 | McCrary |
| 3,783,251 A | 1/1974 | Pavkovich |
| 3,783,288 A | 1/1974 | Barbour et al. |
| 3,946,236 A | 3/1976 | Roberts et al. |
| 4,213,038 A * | 7/1980 | Silverman et al. .......... 235/381 |
| 4,630,274 A | 12/1986 | Schäfer |
| 4,711,996 A * | 12/1987 | Drexler ...................... 235/454 |
| 4,745,268 A * | 5/1988 | Drexler ...................... 235/454 |
| 4,835,372 A | 5/1989 | Gombrich et al. |
| 4,857,713 A | 8/1989 | Brown |
| 4,857,716 A | 8/1989 | Gombrich et al. |
| 5,420,409 A | 5/1995 | Longacre, Jr. et al. |
| 5,482,008 A * | 1/1996 | Stafford et al. ............. 119/174 |
| 5,490,196 A | 2/1996 | Rudich et al. |
| 5,504,796 A | 4/1996 | Da Silveria et al. |
| 5,510,606 A | 4/1996 | Worthington et al. |
| 5,621,779 A | 4/1997 | Hughes et al. |
| 5,661,291 A | 8/1997 | Ahearn et al. |
| 5,663,999 A | 9/1997 | Siochi |
| 5,671,282 A | 9/1997 | Wolff et al. |
| 5,672,154 A | 9/1997 | Sillén et al. |
| 5,754,622 A | 5/1998 | Hughes |
| 5,772,585 A | 6/1998 | Lavin et al. |
| 5,842,976 A | 12/1998 | Williamson |
| 5,845,269 A | 12/1998 | Körtge et al. |
| 5,867,553 A | 2/1999 | Gordon et al. |
| 5,971,279 A * | 10/1999 | Raistrick et al. ....... 235/462.45 |
| 5,979,757 A * | 11/1999 | Tracy et al. ................... 186/56 |
| 6,222,452 B1 * | 4/2001 | Ahlstrom et al. ......... 340/568.1 |
| 6,342,839 B1 * | 1/2002 | Curkendall et al. .......... 340/5.8 |

FOREIGN PATENT DOCUMENTS

JP      406282681 A   * 10/1994

* cited by examiner

Primary Examiner—Karl D. Frech
Assistant Examiner—Allyson Sanders (57) ABSTRACT

A method is provided for verification of the identification of a patient undergoing radiation treatment administered by a treatment technologist in a treatment room. An identifying card for the patient is provided which is part of the patient's treatment file and which includes an identifying optical code capable of being read by an optical reader located within the treatment room. The treatment technologist causes the identifying card of the treatment file to be read by the optical reader in the treatment room, and a characteristic audio signal, previously assigned to the patient and known to the patient and the treatment technologist, is generated in response to the reading of the identifying card when there is a match between the identifying optical code and a stored identifying code for the patient. If an audio signal is generated responsive to reading of the card, both the patient and technologist listen to the signal, and checks are made and treatment of the patient is at least temporarily withheld if the patient and technologist do not agree that the audio signal generated is the characteristic audio signal assigned to the patient. The identifying card also includes a photograph of the patient which is used by the technologist in identifying the patient.

37 Claims, 5 Drawing Sheets

RECORD AND VERIFICATION METHOD AND SYSTEM FOR RADIATION THERAPY

CROSS-RELATIONSHIP TO OTHER APPLICATIONS

The present application claims benefit of priority of U.S. Provisional Application Ser. No. 60/153,243 filed on Sep. 13, 1999; No. 60/155,644 filed on Sep. 24, 1999; No. 60/155,800 filed on Sep. 27, 1999; No. 60/161,416 filed on Oct. 25, 1999; and No. 60/163,084 filed on Nov. 2, 1999.

FIELD OF THE INVENTION

The present invention relates to record and verify systems used in radiation therapy and, more particularly, to an improved record and verification system for such use which includes a number of important features and advantages as compared with prior art systems including those currently in use.

BACKGROUND OF THE INVENTION

By way of background, it is instructive to briefly consider the history of verify and record systems used in connection with radiation therapy treatment of patients using linear accelerators or other megavoltage radiation units. Verify and record systems were originally designed to verify that radiation treatments were set up correctly by the radiation therapy technologist (RTT). This was accomplished through verification that certain key parameters were within predetermined tolerances. The verify and record process has evolved more recently into an automated set-up procedure that emphasizes rapid through-put, while de-emphasizing verification of treatment parameters that previously were set manually by the RTT. Some record and verify systems currently in use actually take control of the manual process by changing physician-selected field sizes, even though the field sizes fall within selected tolerance limits. The trend toward automated systems has led to reduced interaction between the user and the accelerator which has both positive and negative implications. The philosophy of delivering radiation treatment based on an automated set-up model is grounded in the desire to reduce the potential for human error in the set-up process. The downside of the automated or "black box" approach is the disengagement of the RTT from parameter adjustment, i.e., in relieving the RTT of the task of setting the patient treatment parameters through adjustment of the linear accelerator. The negative aspect of this is that if the RTT does not have to set the parameters manually, the RTT is less conditioned to perform the function manually and, therefore, less conditioned to detect errors when these errors occur, whether these errors are dosimetry programming or process errors and whether these errors occur in manual or automated set-up modes. When the RTT is detached from the procedure of manually setting up the patient for treatment, it becomes more difficult for the overall treatment process to recover should the automated process fail. In this regard, when an RTT sets up a patient manually, the RTT "rehearses" the recovery procedure that would be used if the automated primary process should fail. However, when automated set-ups are employed, the RTT is less "rehearsed" in recovering efficiently when the automated process is not available, because such rehearsal of recovery procedures is not integral to automated treatment delivery.

Given current trends in the medical industry, the trend toward automated set-up is irreversible. Further, because of a number of factors including cost pressures, the trend toward staffing reduction is irreversible, at least in the near term. It also appears clear that the electronic record will not totally replace the paper chart, at least not in the near term. In this regard, even if it were proven better for patient care to chart electronically, physician resistance will hinder widespread adoption in the foreseeable future. In general, physicians will not abandon paper charts, either from habit or for medical-legal reasons. Accordingly, the need for maintaining a paper record during implementation of electronic medical record keeping will continue. As a consequence, a further vulnerability of automated radiation treatment systems (in addition to the disengagement of the RTT from the manual recovery process when the automated system is temporarily down), is the potential for mismatches between the electronic record and the paper medical record. These mismatches are commonly due to a failure of the RTT to document treatments in the paper record when the automated system logs the event. The problem of electronic record and paper mismatches is increasing in the specialty of radiation oncology, as reported by clinical medical physicists.

It should be understood that disengagement of the RTT from the manual recovery process increases risk for patient care because the verify and record systems, in many recent configurations, do not check for human error. Record and verify systems, when programmed and executed correctly, can prevent some errors, but not all. Record and verify systems in current use cannot detect human errors when the system itself is the primary process. Additionally, as indicated above, the disengagement of the RTT from linear accelerator parameter adjustment also can disengage the RTT from subtle cues regarding patient identification and radiation field placement. It would be desirable if record and verify systems were configurable to allow automated set-ups at selected times for certain radiation therapy technologists and not for others, such as, for example, when the manual skills of selected RTTs are being assessed. However, the overall trend is clearly toward automated set-up because of the improved throughput which results, as well as the industry-wide momentum toward multi-leaf collimator therapy, which is more optimally performed with automation.

Greater automated throughput can lead to greater risk for other reasons as well. Increased automation means greater potential for a mistake occurring through dose calculation error, with the danger of the error being repeated without prompt detection once the error does occur. The emphasis on throughput also increases the probability of errors in the actual treatment process, characterized by patient identification errors, field sequence errors and field alignment errors. Major preventable ways to harm patients through treatment process failures include (1) treating the wrong patient, i.e., treating a patient with a radiation treatment intended for another patient; (2) treating the right patient, but on a day when the patient is not supposed to receive treatment until other evaluations are performed first (e.g., treating a patient when the patient was supposed to have been seen by the doctor prior to the treatment delivery), and (3) treating the right patient but with the improper treatment set-up, i.e., treating with a wedged field without a wedge, treating with the wrong monitor units (MU) programmed into the accelerator, or treating with the wrong energy. In addition, as described above, in the event that the record and verify device should be temporarily unavailable due to a network, or other, problem, there is a distinct possibility or even an increased probability of parameter selection errors due to human error, because the process of automation can change the behavior of the user. It is noted that more combination chemotherapy with radiation increases toxicity and therefore increases the potential harm that may occur to a patient if the patient receives the wrong treatment or if the patient is treated without proper evaluation before treatment. Moreover, pushing patients to the limit of tissue tolerance increases the potential for adverse events. Automated treatment may increase the possibility of undetected mistakes related to automated set-up, thereby increasing the possibility of patient injury.

As indicated above, the transition to automated treatment system tends to distract the RTTs for a number of reasons. First, and very basically, the new technology creates a new process. Further, the new process diverts RTTs from traditional cross checks in the treatment room. This is true of systems now in use such as the Varis, Impac and Lantis. In addition, visual distractions are created and the RTTs are diverted from paper chart documentation which can be critical in the safe treatment of a patient.

SUMMARY OF THE INVENTION

In accordance with the invention, a record and verify method is provided which addresses the issues discussed above. Among other advantages, the method of the invention assists in verification of patient identity, and, according to an important feature, enlists the patient in the identification process. The invention also documents electronically and manually which RTT was responsible for final parameter verification, including documenting the treated patient, and time of cross-check, and thus avoiding electronic record and paper record mismatches. The patient identification component is installed at a workstation and functions even if the system network is down, thereby maintaining an accountability trail as part of the recovery procedure from network failure.

In accordance with a first aspect of the invention, a method is provided for verification of the identification of a patient undergoing radiation treatment administered by a treatment technologist in a treatment room using a radiation source, the method comprising:

providing an identifying card for the patient including an identifying optical code capable of being read by an optical reader located within the treatment room;

causing the identifying card to be read by said optical reader in the treatment room;

generating a characteristic audio signal, previously assigned to the patient and known to the patient and the treatment technologist, in response to the reading of the identifying card when there is a match between the identifying optical code and a stored identifying code for the patient; and at least temporarily withholding treatment of the patient if the patient and technologist do not agree that any audio signal generated is the characteristic audio signal assigned to the patient.

In an advantageous implementation, the identifying card includes a photograph of the patient and the photograph is used by the technologist in identifying the patient.

Preferably, the identification card is affixed to a treatment file containing treatment data for use by the technologist during treatment, and the card affixed to the treatment file is caused to be read by the technologist thereby ensuring that the technologist takes the treatment file into the treatment room.

In a preferred embodiment, the method further comprises generating an electronic record comprising treatment data associated with the treatment to be administered and including said identifying optical code, causing the identifying optical code of the electronic record to be read by a further optical reader in the treatment room, generating said characteristic audio signal in response to reading of said identifying code of the electronic record, and at least temporarily withholding treatment if the patient and the technologist do not agree that any audio signal generated in response to the reading of the identifying code of the electronic record is the characteristic audio signal assigned to the patient. Advantageously, the optical readers are caused to read the respective optical codes of the card and the electronic record at closely spaced times. Advantageously, the respective optical codes are caused to be read by different technologists. In an advantageous embodiment, the optical readers are located on opposite walls of the treatment room. Preferably, the optical readers are each a part of respective verification stations located at different locations inside of the treatment room and the stored identifying code is stored at a verification workstation located outside of the treatment room and linked to the respective verification stations.

More generally, where there is only one optical reader inside the treatment room, the optical reader is preferably part of a first verification station located inside of the treatment room and the stored identifying code is stored at a verification workstation located outside of the treatment room and linked to the verification station inside the treatment room.

In accordance with a further aspect of the invention which combines some of the features discussed above, a method is provided for identification, and verification of the identification, of a patient undergoing radiation treatment by a radiation source administered by a treatment technologist in a treatment room, the method comprising:

providing a treatment file for the patient to be treated containing a prescribed treatment regimen for the patient;

providing an identifying card affixed to the treatment file and including a photograph of the patient together with an identifying optical code capable of being read by an optical reader located within the treatment room;

causing the identifying card of the treatment file to be read by the optical reader in the treatment room;

generating a characteristic audio signal known to the patient and the treatment technologist in response to the reading of the identifying card when there is a match between the identifying optical code and a stored identifying code for the patient; and providing for checking of the treatment file by the technologist if the patient and technologist do not agree that the audio signal generated is the characteristic audio signal assigned to the patient.

As with the method above, the method of this aspect of the invention preferably comprises generating an electronic record comprising treatment data associated with the treatment to be administered and including said identifying optical code, causing the identifying optical code of the electronic record to be read by a further optical reader in the treatment room, generating said characteristic audio signal in response to reading of said identifying code of the electronic record, and checking the treatment file and at least temporarily withholding treatment by the technologist if the patient and the technologist do not agree that any audio signal generated in response to said reading of the identifying code of the electronic record is the characteristic audio signal assigned to the patient. As above, the optical readers are preferably caused to read the respective optical codes of the card and the electronic record at closely spaced times, and, in an advantageous implementation, are caused to be read by different technologists.

As discussed in connection with the first aspect of the invention, the optical readers are preferably located on opposite walls of the treatment room. More generally, the optical readers are each a part of respective verification stations located at different locations inside of the treatment room and, advantageously, the stored identifying code is stored at a verification workstation located outside of the treatment room and linked to the respective verification stations.

In accordance with yet another aspect of the invention, a record and verify method for use with a radiation therapy system including, located in a treatment room, a radiation treatment device for providing radiation treatment and a treatment monitor for monitoring the treatment provided by the treatment device, the method comprising:

(a) using a patient chart for a patient to be treated to enter treatment data into the treatment monitor;

(b) retrieving stored treatment data for use at a verification monitor;

(c) sending the entered treatment data to the verification monitor for comparison with the stored treatment data;

(d) comparing each data entry of the entered treatment data with a corresponding stored data point of the stored treatment data;

(e) using the verification monitor to output an identifier for each data entry which, based on said comparison, is outside of predetermined tolerances;

(f) correcting, as necessary, the data entered into the treatment monitor based on the output received from said verification monitor to produce corrected treatment data;

(g) generating an electronic record of the corrected treatment data;

(h) using a high speed printer to print the prescribed treatment data on a paper verification sheet;

(i) cross checking the corrected treatment data with previous treatment data;

(j) when the printed paper verification sheet is checked and determined to be accurate, using the radiation treatment device in treating the patient so as to generate actual core treatment data;

(k) printing said actual treatment data on the verification sheet to produce an updated verification sheet;

(l) after completion of a final treatment field of the radiation treatment, reviewing and signing off on the updated verification sheet;

(m) manually entering the actual data obtained from the treatment monitor into the patient's chart and reviewing and signing off on the manual entry of the actual data on the patient's chart; and (n) checking the core treatment data on the printed hard copy against the actual treatment data entered into the patient's chart and, if there is agreement, signing off on the patient's chart and the paper verification sheet.

Preferably, first and second radiation technologists carry out the method, and the first therapist is responsible for steps (a), (c), (f), (j) and (m) and the second therapist is responsible for steps (a), (b), (d), (e), (g), (h), (i), (k), (l) and (n). Advantageously, the first therapist also reviews and signs off on the paper verification sheet upon completion of the method.

In accordance with still a further aspect of the invention, a treatment verification method is provided for use with a radiation therapy system including a radiation treatment device for providing radiation treatment, the method comprising:

a) providing automated and manual set up options for setting of treatment field values for the radiation treatment device wherein, in the automated option, treatment field values are automatically entered as received from a computer at a verification station and wherein, in the manual option, the treatment field values are entered by a technologist at a radiation treatment device workstation;

b) setting different predetermined tolerances based on whether the treatment field values are to be entered in an automated manner by the computer in accordance with said automated option or are to be entered manually by the technologist in accordance with said manual option;

c) selecting between said options and proceeding with the selected option;

d) comparing each data entry for the entered treatment field values with a corresponding stored data point of stored treatment field values; and e) using the verification monitor to output an identifier for each data entry which, based on said comparison, is outside of the predetermined tolerances for the option selected.

In accordance with yet another aspect of the invention, a verification system is provided for use in verification of the identity of a patient about to undergo radiation treatment administered to the patient by radiation source in a treatment room under the control of at least one treatment therapist and monitored by a treatment monitor located in the treatment room, said system comprising:

a verification workstation, located outside of the treatment room, including means for storing a patient identifying code for the patient; and at least one verification station linked to said verification workstation and located within the treatment room at spaced locations on opposite sides of the radiation source, said at least one verification station including an optical reader and means for generating an audible output assigned to the patient, responsive to said optical reader reading a patient identifying code assigned to the patient that matches the patient identifying code stored at the verification workstation.

Preferably, first and second verification stations are provided which are located within the treatment room at spaced locations on opposite sides of the radiation source.

Further features and advantages of the present invention will be set forth in, or apparent from, the detailed description of preferred embodiments thereof which follows.

DESCRIPTION OF THE PREFERRED EMBODIMENTS

Figure 1:
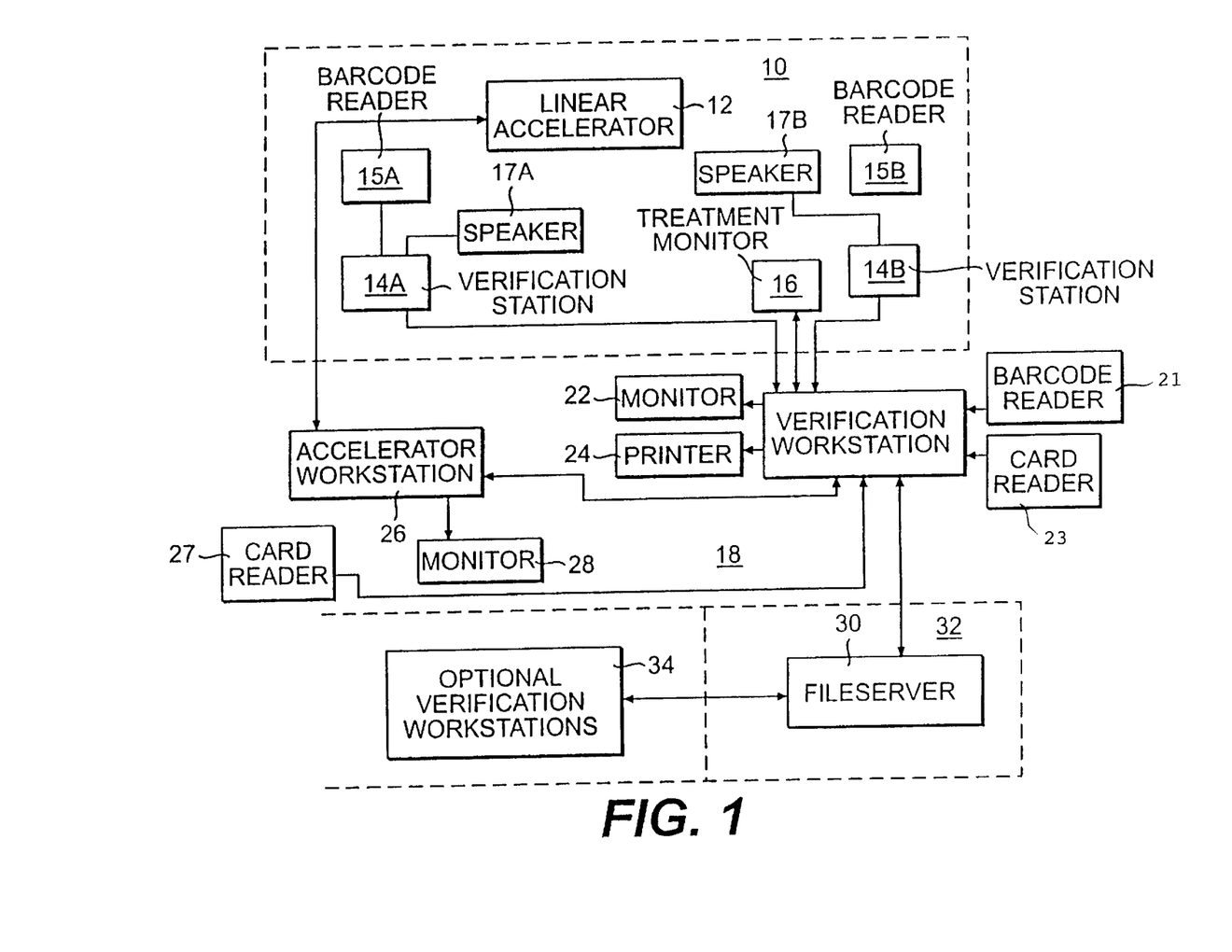
FIG. 1 is a block diagram of a record and verify system in accordance with one preferred embodiment of the invention.

Referring to FIG. 1, a block diagram is provided of one preferred embodiment of the overall system. A treatment room 10 includes a conventional linear accelerator 12 which administers the radiation treatment to the patient and which may be any conventional analog or digital system. Two laser verification stations 14A and 14B are provided in the treatment room 10 along with a treatment monitor 16. The stations 14A and 14B are identical and each preferably includes a respective barcode reader 15A and 15B and a speaker 17A and 17B placed into a single mountable box (not shown). In a preferred embodiment, the verification stations 14A and 14B are located across the treatment room 10 from each other, just beyond the isocenter in the direction of the maze, with the linear accelerator 12 being located between the stations 14A and 14B. Further, the stations 14A and 14B should be situated so that a first technologist, Technologist A, is able to scan a chart or identification card or photograph (not shown) at station 14A on the wall (the left wall is viewed in FIG. 1) while a second technologist, Technologist B, is able to scan a patient's paper verification sheet (as referred to as an electronic sheet, or e-Sheet) at station 14B on the opposite (right) wall. As described below, the e-Sheet is a verification sheet used by the technologist during treatment which shows scheduled and actual treatments. With this setup, each technologist faces towards the gantry of the accelerator 10 and the patient. It is possible to scan the chart on the right rather than the left wall but the e Sheet would then have to be scanned on the left wall scanner. It is understood that while the terms "therapist" are used throughout, the actions described can be carried out by qualified person including qualified doctors, nurses and other hospital personnel and these terms are intended to cover this.

The treatment monitor 16 is used to display the name of the patient and the treatment field values, i.e., the actual fields which are used by the accelerator 10 and which are verified by the verification system. A typical listing of the treatment fields is provided in Table 1 below.

TABLE 1

Treatment Chart Fields and Descriptions

| Number | Description |
|---|---|
| 1 | Hospital Reference Number |
| 2 | Radiation Oncology Number |
| 3 | Protocol Number |
| 4 | Patient's Date of Birth |
| 5 | Referring Doctor's Name, Address, Phone Number and Identification number |
| 6 | Patient's Name |
| 7 | Patient's Address |
| 8 | Patient's Home Phone Number |
| 9 | Patient's Work Phone Number |
| 10 | Patient's Diagnosis |
| 11 | Diagnosis ICU-9 Code |
| 12 | Palliative or Radical |
| 13 | Definitive |
| 14 | Adjuvant |
| 15 | Pre-Op |
| 16 | Post-Op |
| 17 | Chemotherapy |
| 18 | Series Number |
| 19 | Current Date |
| 20 | Site to be treated |
| 21 | Field Description |
| 22 | Rx Dose |
| 23 | Dose per Fraction |
| 24 | Cumulative Dose |
| 25 | Number of Fractions |
| 26 | Energy |
| 27 | Modify |
| 28 | Reassess |

TABLE 1-continued

Treatment Chart Fields and Descriptions

| Number | Description |
|---|---|
| 29 | Stop |
| 30 | Planned Rest |
| 31 | Total Treatments Planned |
| 32 | Physician Signature |
| 33 | Previous Radiation Technologist |
| 34 | Consent Signed |
| 35 | Collimator Size |
| 36 | SAD/SSD |
| 37 | Gantry Angle |
| 39 | Collimator Angle |
| 40 | Drum/Table Angle |
| 41 | Tray/Wedge |
| 42 | Monitor Units |
| 43 | Comments |
| 44 | Port Film Verifications |
| 45 | Inpatient/Outpatient |
| 46 | Elapsed day count for number of treatments (can start at 0) |
| 47 | Radiation Treatment Technologist |
| 48 | Monitor Units |
| 49 | Tumor Dose Cumulative dosage |
| 50 | Physics |

Located outside of the treatment room in a treatment console area 18 is a verification workstation 20 including a verification monitor 22 (e.g., a standard twenty-one inch color monitor) and an associated high-speed printer 24 connected to the verification workstation 20. Also located in area 18 is an accelerator workstation 26 including a card swipe reader 27 and an accelerator monitor 28. The verification workstation 20 basically comprises a personal computer (e.g., NT 4.0) with a keyboard and mouse, which are not illustrated, together with a barcode reader which is shown separately at 21 and a mounted card swipe reader shown separately at 23. The workstation 20 preferably has a minimum of a 10-Megabyte hard drive and 64 Megabytes of memory.

As indicated in FIG. 1, the system also includes a fileserver 30 for the verification workstation 20 which is normally located in a secured room 32. Preferably, there is a TCP/IP connection from the verification station 20, and the file server 30 has enough memory to support at least one verification workstation. The system may also include further, optional verification workstations 34 for running an administration function described below.

For shorthand purposes, the method of the invention will be referred to hereinbelow as the VEEBAT (Verify Easily Electronically Before and After Treatment) method or process, and the verification workstation 20 will also be referred to as the VEEBAT workstation. Moreover, certain terminology will be used which is explained below and which, for the sake of convenience, is capitalized in the description which follows and also defined in the glossary set forth below.

Before consideration of the process in detail, it is noted that the VEEBAT process may take various paths based on its configuration. For example, the configuration may be set up for each patient daily, or just once. The basic configurable parameters are Treatment Fields, technologist, patient and day of the week. Any combination of parameters may be configured. The VEEBAT verification process may be run at the verification (VEEBAT) workstation 20 in an Auto Setup Mode or Manual Setup Mode. The mode refers to how the Treatment Field Values are entered into the accelerometer (PRIMUS) workstation 26. A Manual Setup will have the Treatment Field Values manually entered at the accelerator workstation 26 and an Auto Setup will have the Field Values automatically downloaded from the VEEBAT workstation 20 which electronically sends the treatment parameters automatically to the Accelerator workstation 26. The VEEBAT process may be configured for Auto or Manual Setup based on four parameters: the technologist, the patient, the current day, and the treatment. The technologist parameter has highest priority, i.e., if a particular technologist is configured for VEEBAT Manual only, then Manual will take precedence over Auto setup.

It is noted that the process is configured for two laser verification stations 14A and 14B in the treatment room 10 but may be overridden to operate with one of the laser verification stations if the other laser verification station fails.

Regarding the VEEBAT workstation 20, the process is configured with the single, above-mentioned barcode reader 21 located at the VEEBAT workstation 20 with the VEEBAT Verification Function. The VEEBAT workstation barcode reader 21 functions only to enable access to the application, not to perform the "echo function" (bar-coded photo/e-sheet cross check) described below.

The process is configured to display various reports at VEEBAT startup. The reports are as follows: partial treatment report, cumulative dose reached report, and scheduled patient report. The reports will be displayed on monitor 22 in a scrolling fashion that can be controlled by the person viewing the reports. The partial treatment report will give a listing of patients who received partial treatment the previous day. This report will include the date and the patient's name. The cumulative dose reached report will list patients who have or will exceed their prescribed cumulative dose. The patient's cumulative doses is prescribed by the Radiation Oncologist. The report will include the date and the patient's name. The scheduled patient report will list all patients who are scheduled for treatment on that date. The report will include the patient's name and time of treatment.

Figure 2:
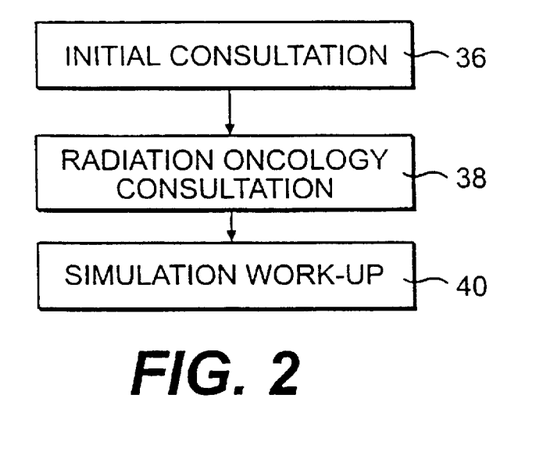
FIG. 2 is a flow chart of an initial consultation sequence involving the patient to be treated.

As an initial matter, referring to FIG. 2, a Patient's File is created on the patient's initial visit. A Patient's File creation consists of the initial consultation and, if advised, the patient's radiation oncology consultation. These steps are indicated in FIG. 2 by blocks 36 and 38. These particular sections of the Patient's File determine if a patient should be treated and, if so, the treatment strategy. A patient's initial consultation determines if radiation therapy is advisable. A radiation secretary creates a Red Folder. The folder contains the patient's referral and medical history. If treatment is advised, a patient is set up for a radiation oncology consultation. Otherwise, the patient's Red Folder will be archived. A radiation oncology consultation determines a patient's prescribed treatment. The patient's initial Red Folder is then moved to a White Folder. The patient's VEEBAT account is created along with a Treatment Folder. The White Folder is a permanent folder for a patient. It will contain the initial Red Folder's contents and radiation oncology consultation.

After completion of a patient's scheduled treatments, all documents in the Treatment Folder are moved to the patient's White Folder. The Treatment Folder is used during the patient's treatments. The folder contains a Treatment Chart, e Sheet, patient set-up photographs and the patient's Polaroid Photo. These items are discussed below. The Treatment Folder also contains the dose calculation work sheets and simulation data, consent form and computer isodose plans, as well as in-vivo dosimetry data. The purpose of using two folders per patient is to reduce conflicts during treatment caused by situations in which radiation treatment technologist (R.T.T.) and nursing personnel simultaneously require access to the medical record. The White Folder and Treatment Foilder are presented to the Radiation Oncologist for telephone calls, patient encounters, dictation, and the like. The Treatment Chart contains a patient's original prescription and treatment schedule signed by the Radiation Oncologist. The chart is used during treatment by the Technologist to manually enter Treatment Field Values into the accelerator workstation 26. Typical Treatment Field Values are set forth in Table 2 below.

TABLE 2

| Number | Name |
| --- | --- |
| 1 | Monitor Units |
| 2 | Jaw/Collimator Size |
| 3 | Collimator Angle |
| 4 | Gantry Angle |
| 5 | Table Drum Angle (optional) |

The e Sheet is, as mentioned above, used during the verification process to store prescribed and actual Treatment field Values. A new Treatment Folder will receive a blank e Sheet. A barcode is attached to the e Sheet. A detailed listing of fields and descriptions is provided above. Each Treatment Folder contains patient's set-up photographs to indicate the area for treatment along with tattoo markings. Each Treatment Folder also contains a patient's Polaroid Photo. This photograph or picture is used during the verification process to help insure the Treatment Folder belongs with the patient being treated. A barcode is attached to the Polaroid Photo.

The method and system of the invention lends itself well to accounting and billing tasks. As a first step, the patient's VEEBAT Account is created. The account is used in the verification procedure during treatments. The account is generated on a VEEBAT verification workstation 20 (or one of the optional workstations 34) using the VEEBAT Administration Function. A typical chart with a detailed listing of fields and descriptions is provided in Table 3 below. Barcodes on the patient's e Sheet and Polaroid photo will be associated to the patient's VEEBAT Account. As described in more detail below, the patient will be assigned a unique audio signal (e.g., a three tone audio signal in the exemplary embodiment under consideration) that will be used for audio verification by each of the patient, Technologist A and Technologist B in the Treatment Room prior to treatment.

TABLE 3

| Patient Information | |
| --- | --- |
| RT #: | |
| Patient Name: | |
| Date of Birth: | |
| Referring MD: | (link into UPIN chart) |
| City of Residence: | |
| Telephone No (home): | |
| Telephone No (work): | |
| Diagnosis: | {ascii text} |
| ICD 9 Code: | (link into ICD 9 chart) |
| Chemotherapy | y/n |
| Hormone Therapy | y/n |
| Bar code - Polaroid photo: | |
| Bar code - e Sheet: | |
| (link to actual treatment delivered) | |

A simulation system provides access to a comprehensive library of treatment strategies, including treatment protocols, simulation checklists, guides on how to order tests, and test rationale and, as indicated by block 40 in FIG. 2, a simulation work-up can be provided as part of the initial consultation process.

Turning now to the actual patient treatment process which is one key aspect of the present invention, and referring to FIGS. 3A to 3D, the patient arrives for treatment as indicated by block 42 and checks in with the receptionist. Technologist A obtains the patient's Treatment Folder, scans the patient's Polaroid Photo at the treatment console or workstation 20 to initiate VEEBAT Verification Function, and ensures the patient matches the patient Polaroid Photo, as indicated by block 44. If there is a match, Technologists A and B escort the patient to treatment room 10 (block 46). Technologist B obtains the patient's e Sheet from the Treatment Folder. Technologist A scans the photo at the barcode reader 15A of the verification station 14 (block 48). If Technologist A is unable to scan the photo for any reason, a Supervisor will be requested to help resolve the problem. Once the photo has been successfully scanned, the VEEBAT verification workstation 20 will associate the photo with the patient's VEEBAT Account in the VEEBAT Database (block 50). If the patient's VEEBAT Account is not found, an Audio Error Signal ("beep") will be emitted and a Supervisor will be required to resolve the problem.

Figure 3A:
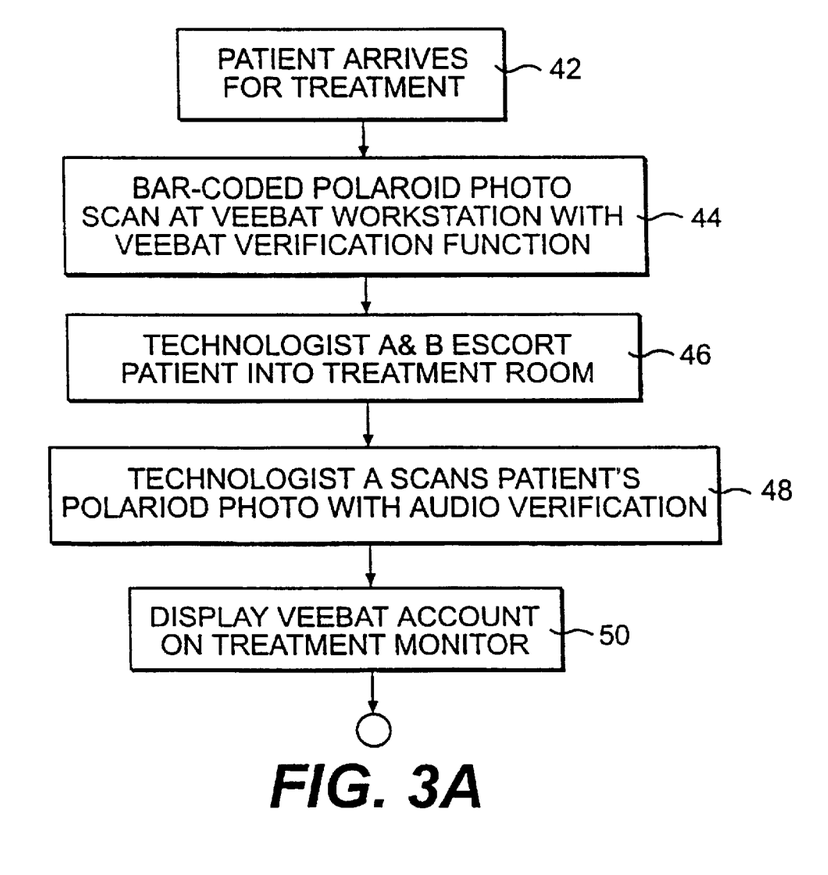
FIGS. 3A, 3B, 3C and 3D, taken together, are a flow chart of a record and verify method in accordance with one preferred embodiment of the invention.

Considering in more detail the steps which take place, after Technologists A and B escort the patient into Treatment Room 10, the patient is correctly positioned on treatment table. Technologist A proceeds to either laser verification station 14A or 14B. Technologist B proceeds to other laser verification station. It will be assumed here that Technologist A is at station 14A and Technologist B is at station 14B. Technologist A then scans barcode on the patient's Polaroid Photo at the barcode reader 15A (block 48). The barcode is passed to the VEEBAT Verification Function at the verification workstation 20 to ensure the barcode matches the Polaroid Photo bar code that was just scanned outside the treatment room at the verification workstation 20. If valid, the patient's audio signal is emitted at the verification station 14A. If the Technologist fails to scan the Patient's Polaroid Photo at the VEEBAT verification workstation 20, an Audio Error Signal is issued. This will require the Technologist to go back to the VEEBAT verification workstation 20 to scan the Patient's Polaroid Photo bar code to initiate the VEEBAT Verification Function. Further, if the bar code scanned at barcode reader 15A of verification workstation 14A is a valid VEEBAT account bar code, but does not match the bar code previously scanned at the VEEBAT verification workstation 20, an audio Error Signal will be emitted in this case as well and a Supervisor will be required to resolve the problem. If the patient's e Sheet bar code is scanned first, i.e., if the bar code scanned is the e Sheet bar code associated with the current VEEBAT Account, an audio Warning Signal is issued and the system waits for the Patient's Polaroid Photo bar code to be scanned. If the bar code is not a valid VEEBAT bar code, it will be considered to be a read error. The VEEBAT verification workstation will emit an audio Warning Signal and wait for a re-scan. Considering other potential failures, if the bar code is found but the patient cannot be treated, an audio Error Signal is issued. Again a Supervisor is required to resolve this problem. If the patient's cumulative dose exceeds or will exceed the patient's prescribed dose, a stop order is issued. In this regard, the patient's VEEBAT Account has a stop treatment flag set, which is determined by the Radiation Oncologist.

The patient name and scheduled Treatment Field Values from the selected VEEBAT Account are displayed on the treatment monitor 16 in a large font for easy readability. Also, if a port verification film (PVF) is scheduled, a reminder will appear on the treatment room monitor 16 to remind the technologists. Technologists A and B will visually verify that the name displayed on the monitor matches the patient's name. If not, a Supervisor shall be called to resolve the problem.

Figure 3B:
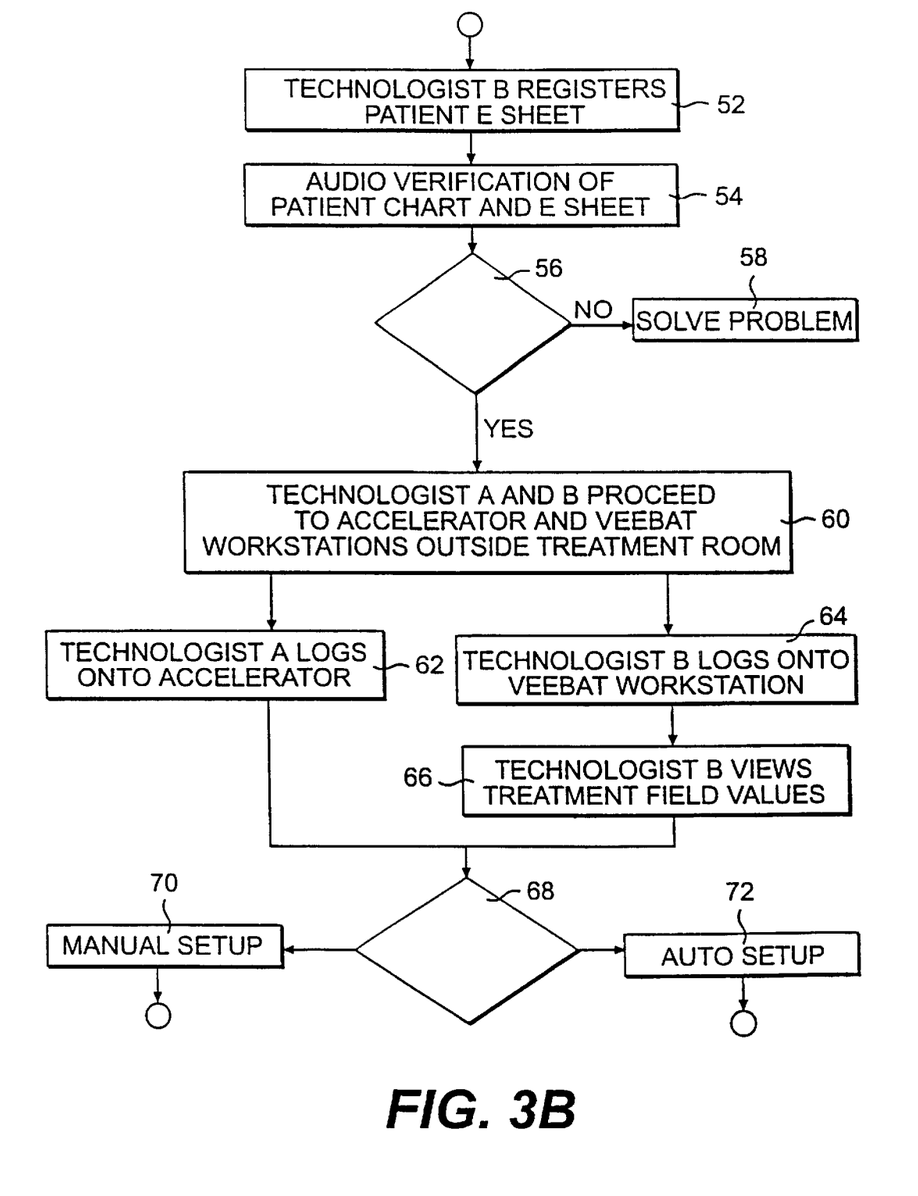

Referring to FIG. 3B, in the next step, Technologist B scans the patient's e Sheet bar code, as indicated by block 52 at barcode reader 15B of verification workstation 14B. The VEEBAT Verification Function then verifies that the bar code is assigned to the patient's VEEBAT Account. Verification of the patient chart and e Sheet is then provided. As shown by decision diamond 56, if valid, i.e., if there is a match, the patient's audio signal is emitted. If there is no match, an audio Error Signal is emitted and a Supervisor is required to resolve this problem (block 58). When the tone is emitted, Technologist A, Technologist B, and the patient all verify that the audio signals emitted from Verification Stations 14A and 14B are the same. The use of identification signals such as unique audio signals is an important aspect of the invention and, among other advantages, provides a comfort level for the patient that is not available with other methods and systems. If anyone questions the comparison of the audio signals, a Supervisor is required to resolve this issue. This aspect of the invention, i.e., the use of an audio signal unique to the patient and the requirement that the patient and the technologist (or technologists) in attendance all verify the signal, is discussed in more detail below.

Next, as shown by block 60, Technologist A proceeds to accelerator workstation 26 and Technologist B proceeds to the VEEBAT verification workstation 20 to access the VEEBAT Verification Function. Technologist A logs onto the accelerator workstation 26 (block 62) and uses the card swipe reader 27 located on the accelerator workstation 26 to register with the Verification Function of the VEEBAT verification workstation 20. If Technologist A is unknown or does not have privilege to apply treatment, then the Verification Function of the verification (VEEBAT) workstation 20 will display a message at the VEEBAT workstation indicating the discrepancy. A Supervisor will be required to resolve this problem.

Technologist B logs onto the VEEBAT verification workstation 20 by using the card swipe reader 23 located on the VEEBAT verification workstation 20 that uses the VEEBAT Verification Function (block 64). If Technologist B is unknown or does not have privilege to apply treatment, then the Verification Function will display a message on the VEEBAT verification workstation 20 indicating the discrepancy. A Supervisor will be required to resolve this problem. Technologist B then views the scheduled Treatment Field Values for the patient at the VEEBAT workstation 20 (block 66).

Figure 3C:
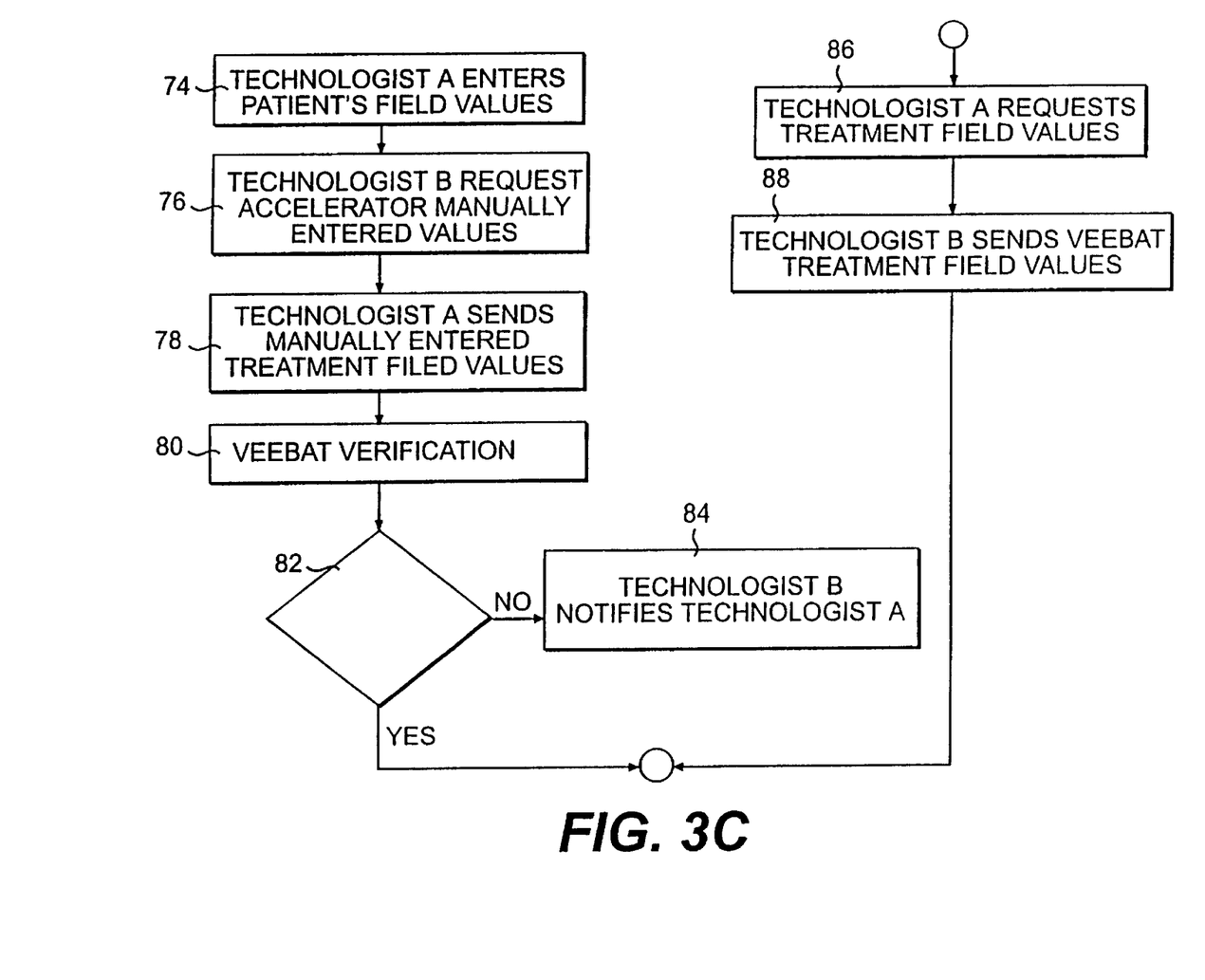

As indicated by decision diamond 68, and was discussed above, the VEEBAT process can be configured for Manual Setup or Auto Setup. If the former confirmation is chosen, as indicated by block 70, the steps set forth at the left side of FIG. 3C are taken. Considering these steps, Manual Setup first requires that Technologist A manually enter Treatment Field Values as indicated on the patient's Treatment Chart at the accelerator workstation 26. The Treatment Field Values are then automatically verified at the VEEBAT workstation 20 by the VEEBAT Verification Function against the patient's prescribed treatment. As shown by block 74, Technologist A manually enters Treatment Field Values indicated on the patient's Treatment Chart at the accelerator workstation 26. Technologist B then places the VEEBAT Verification Function in ready-to-receive mode. Technologist B verbally requests Technologist A to electronically send the patient's Treatment Field Values that were manually entered at the accelerator workstation 26 to the VEEBAT workstation 20 (block 76). The accelerator (PRIMUS) workstation 26 electronically sends the data to the VEEBAT workstation 20 when Technologist A presses a designated button (e.g., the "ACCEPT" button) on the accelerator keyboard (block 78). The VEEBAT workstation Verification Function will only receive values from the accelerator workstation 26 when the VEEBAT verification workstation is in the ready-to-receive mode. At any time, Technologist B has the option to cancel the ready-to-receive mode, thus returning the VEEBAT verification workstation 20 to its previous state.

As indicated by block 80, the VEEBAT Verification Function, after receiving the accelerator values that have been entered, will then verify all patient's Treatment Field Values and confirm that all values are within predetermined tolerances. If any Treatment Field Values are not within the predetermined tolerances, the VEEBAT verification workstation will give an audio Warning Signal ("beep") and display an asterisk beside each field that is not within the predetermined tolerance. If all fields are within predetermined tolerance (i.e., when the output of decision diamond 82 is "yes"), the method or procedure continues as described below.

As indicated by decision diamond 82, if accelerator manual values are incorrect, Technologist B advises Technologist A to reenter any Treatment Field that was flagged at the VEEBAT workstation with an asterisk (block 84). The processing is then repeated. If Technologist A intentionally enters in a value that is not consistent with the predetermined tolerance for any of patient's Treatment Fields, a Supervisor override is required.

Referring to the right side of FIG. 3C, the Auto Setup configuration electronically sends values from the patient's VEEBAT Account through the VEEBAT verification workstation 20 to the Accelerator workstation 26. In this regard, in the specific implementation under consideration, Technologist A places the accelerator workstation in a ready-to-receive mode by depressing a specific key (e.g., the F5 key) on the accelerator keyboard (not shown). Technologist A verbally requests Technologist B to electronically send the patient's Treatment Field Values(block 86). Technologist B, by depressing a download key, sends the requested patient's Treatment Field Values to the accelerator workstation 26.

Figure 3D:
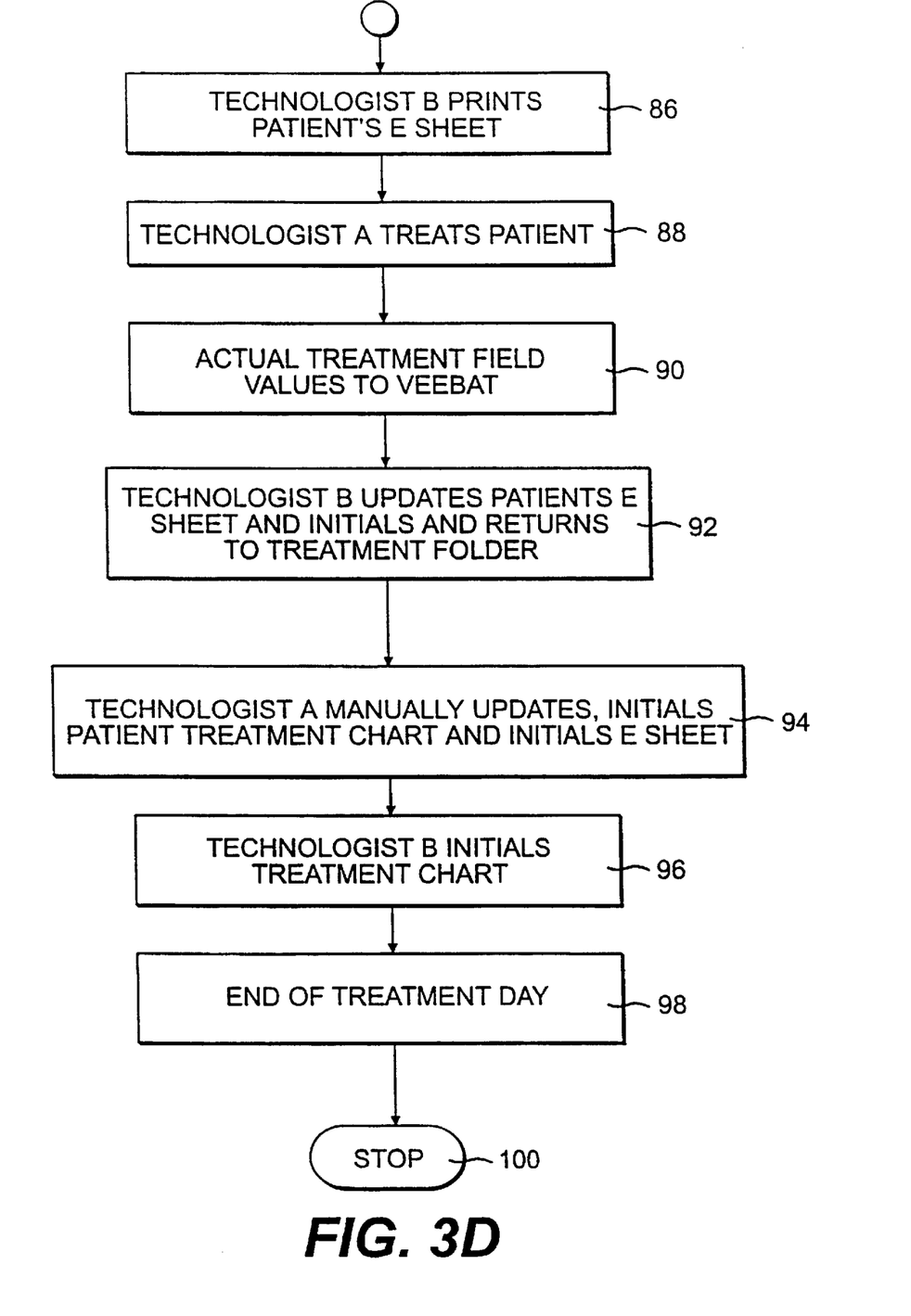

It is noted that in accordance with a further aspect of the invention different tolerances are provided for Manual Setup and Auto Setup. In Auto Setup, relatively tight tolerances are provided so that, for example, the gantry angle tolerance may be ±1°. Although the automated operation has its advantages, it is important in some circumstances to provide a manual approach wherein the RTT manually sets the Treatment Field Values. Such a manual approach can be customized to the requirements of the patient over time and, in this regard, the Treatment Field Values may be changed over the course of treatment during the day. As a consequence, the tolerances set here should be relatively wider to accommodate the manual approach and, for example, the gantry angle tolerance may set at ±5°. Thus the VEEBAT function provides a different set of tolerances for Manual Setup versus Auto Setup. Referring to FIG. 3D, which depicts the remainder of the method or procedure, which is common to both the Manual Setup and Auto Setup, Technologist B requests the VEEBAT verification workstation 20 to print a treatment entry on the patient's e Sheet at printer 24 (block 86), i.e., the date, energy, MU and wedge (i.e., the number of the wedge used, if any) for each prescribed/scheduled Treatment Field of the current treatment session. This occurs before the first treatment field for this treatment session. If this is not the patient's initial treatment session, the technologist will compare the printed values on the e Sheet to the previous treatment values (i.e. the line above on the chart). If the verification fails, a Supervisor is informed of any discrepancies.

As indicated by block 88, Technologist B next gives the Accelerator workstation 26 permission to treat the patient via the VEEBAT verification workstation 20 and verbally informs Technologist A to proceed with treatment. If, during treatment, the accelerator 12 fails to give a complete treatment due to mechanical failure or technologist intervention, Technologist A may "fix" the problem and resume treatment until treatment is complete. However, if Technologist A is unable to complete treatment due to equipment failure or human decision, a Supervisor should, at a later time but prior to next treatment, manually write in the make-up dosage in the right margin of the Treatment Chart and override the patient's VEEBAT Treatment Schedule.

Next, as indicated by block 90, the actual Treatment Field Values are sent to the VEEBAT verification workstation 20 from accelerator workstation 26. The VEEBAT Verification Function updates the screen with actual treatment dose delivered and saves the values to the VEEBAT fileserver 30. If this is not the last treatment beam of the session, the technologists return to the treatment room and set up the patient for the next treatment field. If this is the last treatment, as shown by block 92, Technologist B submits the e Sheet to print the actual monitoring units (MU) on the same row of the e Sheet where the prescribed/scheduled Treatment Field Values are printed on the e Sheet in step 86 above. Thus, in a preferred embodiment, the e Sheet will include columns of entry spaces for the date, energy, wedge and MU, and for initialing by the Technologist or therapist. Such an e Sheet has important advantages because of its simplicity. An asterisk will be printed beside each Treatment Field that received a MU value outside the predetermined tolerance range. If one or more Treatment Field MUs were printed with asterisks, an asterisk will also be printed in the far right-hand column for the day's treatment. This asterisk indicates any discrepancies to the reviewing Physicist. Technologist B should initial the e Sheet at the appropriate session entry space and hand it to technologist A to initial and return to the patient's Treatment Folder (block 92). Technologist A enters the actual Treatment Field Values as shown on the accelerator workstation screen on the Patient's Treatment Chart (block 94). Technologist A then initials the Patient's Treatment Chart at the appropriate session line and hands it to Technologist B. Technologist B initials the Patient's Treatment Chart at the appropriate session line and returns it to the Patient's Treatment Folder (block 96).

Referring to block 98, at the end of the day, various reports can be requested. The reports are generated at a VEEBAT verification workstation 20 using the VEEBAT Administration Function. These reports can include a report of patients who received partial treatment. This report will list each patient that received a smaller dose for that day than was prescribed for that day. This report shall contain patient names and RT numbers.

The reports may also include a list of scheduled patients who were not treated. Such a report will list each patient who was scheduled for treatment that day but did not receive treatment that day for any reason. This report shall also contain the Patient names and RT numbers.

Statistics can also be output for the following treatment types: electron, photon, simple, intermediate and/or complex.

A billing summary can also be produced. This report will list charge codes for each patient treatment as well as patient's name, and concurrent chemotherapy or hormone treatments, if any.

A report can be generated on any information maintained in the VEEBAT database which is located on Fileserver 30.

Considering in more detail the use of a photograph of the patient in generating distinctive audio output, in a preferred embodiment, a photograph of the face of the patient with an identifying barcode is taped or otherwise affixed to the inside front jacket of the Treatment Chart, although the photograph and bar code can take other forms and be printed or mounted on other media. When the chart photograph, with barcode, is scanned by the barcode reader of the corresponding laser verification station in question (station 14A in the example above), a suitable audio output which is uniquely associated with, i.e., specific to, the particular patient is emitted by the speaker (not shown) of the station. Conventional methods are available to generate a specific audio output in response to a corresponding triggering input, including computer generation of sounds or tones. As described above, verification station 14B is used to scan the patient's e sheet. In the specific exemplary embodiment under consideration, the audio output is an audio signal which takes about one second to complete. Of course, while a soothing tone sequence is preferred and has important advantages, other audio outputs can be used including a recording of the patient's name.

In an exemplary embodiment wherein three sequence of tones comprising the three tone chord is determined at simulation by the patient's RT number. For example, departments with different lengths of patient identifying numbers can adjust with a different range of octaves. Four digit departments can use a different octave for the first digit. Five digit departments can use a different octave for the first and second digit. Digits which begin with eight or nine can use sharps or flats as the first digit.

As indicated above, in the specific application under consideration, the second therapist, Therapist B, scans the patient's e Sheet at barcode reader 15B at laser verification station 14B located inside the treatment room on the opposite wall from station 14A, and a confirmatory audio signal emitted from the speaker 17B at station 14B is reassuring the staff that the Treatment Chart's face photo matches the e Sheet. This creates an opportunity to detect whether another patient's e Sheet has been inadvertently placed in the Treatment Chart. The audio signal emitted at station 14A obtained by scanning the patient's Treatment Chart should match precisely the audio signal emitted from the speaker 17B at station 14B. This process of scanning the Treatment Chart, producing a patient specific audio signal and then confirming the audio signal by scanning the e Sheet and producing the audio signal again is referred to herein as "echoing." Echoing is performed most efficiently when the e Sheet is scanned almost immediately after the Treatment Chart is scanned and thus generates its audio signal.

The sequence of Treatment Chart audio signal activation, followed by e Sheet tone activation, confirms that the Treatment Chart photo barcode is the same as the e Sheet barcode. If the wrong Treatment Chart is selected, the patient should notice a non-familiar audio signal, providing a self-managing dimension to the VEEBAT process. Patients often report to their radiation oncology caregivers that they count the seconds of treatment or that they occasionally report perceived changes in the sound of the accelerator as it delivers the radiation treatment. The confirmatory audio signal should reassure anxious patients, while allowing an opportunity for wrong audio signal to be noticed by a patient. This provides an added incentive for the staff to select the correct Treatment Chart since the patient also participates in the cross checking process.

In accordance with a further feature of this aspect of the invention, subsequent fields will be confirmed by a repeat of the last tone and the next tone of the second field, the last tone and the two next tones for the third field, and the last tone and three consecutive tones for the fourth field. Variations of this tone feedback process could be used for three dimensional conformal therapy. Certainly, many patients are already primed for audible feedback and the use of audio confirmation should be of help to patients as well as the staff. The foregoing sequence of barcode scanning brings up the patient's VEEBAT parameters which may then be downloaded for Auto Setup or Manual Setup, followed by verification before and after treatment as described above. This verification process provides a number of important advantages which will now be described.

First, two therapists are encouraged to enter the room with the patient and the Treatment Chart, maximizing the opportunity for satisfactory visual crosscheck. Both therapists are encouraged to enter the room because efficiency inside the room will be rewarded by bringing up the VEEBAT parameters more rapidly, either for Manual Setup verification or Auto Setup. As indicated previously, two therapists are not required to enter the room but if only one therapist enters the room, she or he will still have to bring the Treatment Chart so that no charts will be left on the counter outside the treatment room. Moreover, the lone therapist will still have to set up the patient properly, then activate the VEEBAT queue with the e Sheet at the right wall, i.e., at station 14B, as viewed in FIG. 1.

Further, with two therapists Therapist A must be with the patient at the left side of Accelerator 12 before the audio signal can be generated. The Treatment Monitor 16 and the VEEBAT monitor 22 will display simplified patient parameters only after the e Sheet is properly scanned and the second audio signal is generated at station 14B. Typically, the simplified parameters are defined as a field number, i.e., 1) AP pelvis/prostate, 2) R lat pelvis/prostate, 3) PA pelvis/prostate, and 4) L lat. If Auto Setup has been approved by the Radiation Oncologist for the treatment of the patient, then treatment monitor 16 (in treatment room 10), and VEEBAT monitor 22 (on the treatment counter) will display the simplified patient parameters with, e.g., red letters. If the patient is being treated using Manual Setup, then the corresponding screens will display the simplified patient parameters with different, e.g., white, letters.

Because the display will also appear on VEEBAT monitor 22 at the treatment counter in area 18 which is not in treatment room 10, this provides advanced queuing for treatment, thereby minimizing delays outside the room due to delays in calling up the parameters after the patient's alignment has been visually cross-checked.

In an advantageous implementation, patients are assigned a new RT number and bar code for each course of radiation therapy. In an advantageous implementation, if a patient returns to the radiation oncology department in the future, e.g., for a second course of radiation therapy several years in the future, a fourth note will be added before the three-tone chord assigned for the current year, creating a new four-note chord. This serves as an audible reminder to the staff that the patient has had a previous course of therapy, and that they should watch our for possible overlap of the current field with the prior fields. A third course of therapy will generate a fifth note. In other words, in this implementation, there will be two tones, followed by a pause, followed by the three-tone chord for the current course of radiation treatment. It is more difficult to audibly discriminate longer sequences of tones, and this approach takes advantage of this. The greater the number of prior courses of radiation the patient has had in prior years, the more difficult it is for the therapist to feel comfortable with alpha-beta confirmations, and the more motivated he or she will be to go back to the records to verify lack of overlap with the current fields.

One very important advantage of the verification method and system of the invention is that its primary method of supplemental communication is audio, thereby eliminating the use of additional visual distractions that might divert the attention away of the therapists from the patient's Treatment Chart and actual treatment setup and visual cross-check. This approach also provides for more efficient queuing of the server verification data to the monitor outside the treatment room, so as to provide time for therapists to perform an official verification, followed by treatment, immediately upon reaching the treatment counter or console. Overall, the invention should make treatments faster and more accurate than with existing record and verify systems, because the invention enhances and verifies efficient manual process without altering therapist behavior.

| | |
|---|---|
| Accelerator | The actual accelerator located in the treatment room. |
| Accelerator System | The Accelerator Workstation and the Accelerator. |
| Accelerator Workstation | Part of the Accelerator System, Consists of monitor, special keyboard, and computer. Location is outside the room of the Accelerator. |
| Auto Setup | The Accelerator System receives its Treatment Field Values from the VEEBAT Verification Function |
| Bar Code | A label on the Polaroid Photo and e Sheet used to identify electronically the patients VEEBAT Account. |
| Card Swipe | Device used to identify user by badge number |
| Cumulative Dose | Total Radiation received |
| e Sheet | Verification sheet used by Technologist during treatment showing scheduled and actual treatments |
| Error Signal | Audio tone emitted from VEEBAT Workstation when an error requiring a Supervisor is required. |
| ICD-9 Codes | Used to categorize patients cancer location |
| Laser Verification Station A | A verification station located in the treatment room. Consist of a bar code reader and a speaker. Used by Technologist A to read a patients bar coded Patients Chart. |
| Laser Verification Station B | A verification station located in the treatment room consisting of a bar code reader and a speaker. Used by Technologist A in reading a patient's bar coded Patients Chart. |
| Manual Setup | The Accelerator System receives its Treatment Field Values from the Accelerator Workstation |
| MU | The length of a treatment (Monitor Units). |
| Patients File | Patients Treatment Chart, e Sheet, and Polaroid Photo |
| PC | Personal Computer. |
| PVF | Port Verification Film |
| Polaroid Photo | Picture of Patient |
| Radiation Oncologist | Physician |
| Red Folder | A patients tolder untii treatment is determined |
| RT | Radiation Oncology Number. |
| RTT | Radiation Therapy Technologist |
| RTT | Radiation Therapy Technologist (Technologist) |
| Setup Room | Room where Technologist A and B run the Accelerator and VEEBAT Systems |
| Radiation Oncology | Work done with the simulator to determine a |

-continued

| | |
|---|---|
| Consultation | patients treatment |
| Supervisor | Senior Radiation Technologist |
| TOP/JP | Network communication protocoJ. |
| Technologist A | Technologist responsible for VEEBAT Verification during treatment. |
| Technologist B | Technologist responsible for Accelerator Workstation during treatment. |
| Total Dose | Total prescribed dose |
| Treatment Field Values | Actual fields used by the Accelerator and verified by the VEEBAT Verification Function. See Appendix A for list. |
| Treatment Folder | Folder used by Technologist during treatment |
| Treatment Monitor | A monitor located in the treatment room used to show a patients name and Treatment Field Values |
| VEEBAT Account | Electronic data entered via VEEBAT Workstation with VEEBAT Administration Function. |
| VEEBAT Administration Function | A program running on a VEEBAT Workstation. The program is used to create and access patients VEEBAT accounts stored on the VEEBAT fileserver. The program also provide various report generation functions and administrative functions (i.e. System Backup) |
| VEEBAT Fileserver | A workstation with houses the VEEBAT Database. |
| VEEBAT Process | Verify Easily Electronic Before and After Treatment Process |
| VEEBAT System | The actual components used to implement the VEEBAT Process |
| VEEBAT Verification Function | A program running on a VEEBAT Workstation. The program is used to provide a verification before and after treatment |
| VEEBAT Workstation | A workstation with monitor, keyboard, mouse, CPU, bar code reader, and card swipe. The workstation provides the VEEBAT Administration and/or Verification Function. |
| Warning Signal | Audio tone emitted from VEEBAT Workstation when an error occurred but does not require a Supervisor. |
| White Folder | A patients permanent folder during and after treatment |

Although the invention has been described above in relation to preferred embodiments thereof, it will be understood by those skilled in the art that variations and modifications can be effected in these preferred embodiments without departing from the scope and spirit of the invention.

What is claimed:

1. A method of verification of an identification of a patient undergoing radiation treatment administered by a treatment technologist in a treatment room using a radiation source, said method comprising:

providing an identifying card for the patient including an identifying optical code capable of being read by an optical reader located within the treatment room;

causing the identifying card to be read by said optical reader in the treatment room;

generating a characteristic audio signal, previously assigned to the patient and known to the patient and the treatment technologist, in response to the reading of said identifying card when there is a match between the identifying optical code and a stored identifying code for the patient; and at least temporarily withholding treatment of the patient if the patient and technologist do not agree that any audio signal generated is the characteristic audio signal assigned to the patient.

2. A method according to claim 1 wherein said identifying card includes a photograph of the patient and the photograph is used by the technologist in identifying the patient.

3. A method according to claim 1 wherein said identifying card is affixed to a treatment file containing treatment data for use by the technologist during treatment, and the card affixed to the treatment file is caused to be read by the technologist thereby ensuring that the technologist takes the treatment file into the treatment room.

4. A method according to claim 3 further comprising generating an electronic record comprising treatment data associated with the treatment to be administered and including said identifying optical code, causing the identifying optical code of the electronic record to be read by a further optical reader in the treatment room, generating said characteristic audio signal in response to reading of said identifying code of the electronic record, and at least temporarily withholding treatment if the patient and the technologist do not agree that any audio signal generated in response to said reading of the identifying code of the electronic record is the characteristic audio signal assigned to the patient.

5. A method according to claim 4 wherein said optical readers are caused to read the respective optical codes of the card and the electronic record at closely spaced times.

6. A method according to claim 5 wherein said respective optical codes are caused to be read by different technologists.

7. A method according to claim 6 wherein the optical readers are located on opposite walls of the treatment room.

8. A method according to claim 4 wherein said optical reader and said further optical reader are a part of respective verification stations located inside of the treatment room and the stored identifying code is stored at a verification workstation located outside of the treatment room and linked to said respective verification stations.

9. A method according to claim 1 wherein said optical reader is part of a first verification station located inside of the treatment room and the stored identifying code is stored at a verification workstation located outside of the treatment room and linked to the first verification station.

10. A method according to claim 9 wherein the identifying card includes a photograph of the patient and the photograph is used by the technologist at the verification workstation in storing the stored identifying code.

11. A method of identification, and verification of the identification, of a patient undergoing radiation treatment by a radiation source administered by a treatment technologist in a treatment room, said method comprising:

providing a treatment file for the patient to be treated containing a prescribed treatment regimen for the patient;

providing an identifying card affixed to the treatment file and including a photograph of the patient together with an identifying optical code capable of being read by an optical reader located within the treatment room;

causing the identifying card of the treatment file to be read by said optical reader in the treatment room;

generating a characteristic audio signal known to the patient and the treatment technologist in response to the reading of said identifying card when there is a match between the identifying optical code and a stored identifying code for the patient; and providing for checking of the treatment file by the technologist if the patient and technologist do not agree that the audio signal generated is the characteristic audio signal assigned to the patient.

12. A method according to claim 11 further comprising generating an electronic record comprising treatment data associated with the treatment to be administered and including said identifying optical code, causing the identifying optical code of the electronic record to be read by a further optical reader in the treatment room, generating said characteristic audio signal in response to reading of said identifying code of the electronic record, and checking the treatment file and at least temporarily withholding treatment by the technologist if the patient and the technologist do not agree that any audio signal generated in response to said reading of the identifying code of the electronic record is the characteristic audio signal assigned to the patient.

13. A method according to claim 12 wherein said optical readers are caused to read the respective optical codes of the card and the electronic record at closely spaced times.

14. A method according to claim 13 wherein said respective optical codes are caused to be read by different technologists.

15. A method according to claim 14 wherein the optical readers are located on opposite walls of the treatment room.

16. A method according to claim 12 wherein said optical reader and said further optical reader are a part of respective verification stations located at different locations inside of the treatment room and the stored identifying code is stored at a verification workstation located outside of the treatment room and linked to said respective verification stations.

17. A method according to claim 11 wherein said optical reader is part of a first verification station located inside of the treatment room and the stored identifying code is stored at a verification workstation located outside of the treatment room and linked to the first verification station.

18. A record and verify method for use with a radiation therapy system including, located in a treatment room, a radiation treatment device for providing radiation treatment and a treatment monitor for monitoring the treatment provided by the radiation treatment device, said method comprising:

(a) using a patient chart for a patient to be treated to enter treatment data into the treatment monitor;

(b) retrieving stored treatment data for use at a verification monitor;

(c) sending the entered treatment data to the verification monitor for comparison with the stored treatment data;

(d) comparing each data entry of the entered treatment data with a corresponding stored data point of the stored treatment data;

(e) using the verification monitor to output an identifier for each data entry which, based on said comparison, is outside of predetermined tolerances;

(f) correcting, as necessary, the data entered into the treatment monitor based on the output received from said verification monitor to produce corrected treatment data;

(g) generating an electronic record of the corrected treatment data;

(h) using a high speed printer to print prescribed treatment data on a paper verification sheet;

(i) cross checking the corrected treatment data with previous treatment data, if any;

(j) when the printed paper verification sheet is checked and determined to be accurate, using the radiation treatment device in treating the patient so as to generate actual core treatment data;

(k) printing said actual treatment data on the paper verification sheet to produce an updated verification sheet;

(l) after completion of a final treatment field of the radiation treatment, reviewing and signing off on the updated verification sheet;

(m) manually entering the actual data obtained from the treatment monitor into the patient's chart and reviewing and signing off on the manual entry of the actual data on the patient's chart; and (n) checking the core treatment data on the updated verification sheet against the actual treatment data entered into the patient's chart and, if there is agreement, signing off on the patient's chart and the updated verification sheet.

19. A method according to claim 18 wherein first and second radiation technologists carry out the method, and wherein the first therapist is responsible for steps (a), (c), (f), (j) and (m) and the second therapist is responsible for steps (a), (b), (d), (e), (g), (h), (i), (k) and (n).

20. The method according to claim 19 wherein the first therapist also reviews and signs off on the hard copy upon completion of the method.

21. A verification system for use in verification of an identity of a patient about to undergo radiation treatment administered to the patient by radiation source in a treatment room under control of at least one treatment technologist and monitored by a treatment monitor located in the treatment room, said system comprising:

a verification workstation, located outside of the treatment room, including means for storing a patient identifying code for the patient; and at least one verification station linked to said workstation and located within the treatment room, said at least one verification station including an optical reader and means for generating an audible output assigned to the patient, responsive to said optical reader reading a patient identifying code assigned to the patient that matches the patient identifying code stored at said verification workstation.

22. A system according to claim 21 wherein said at least one verification station comprises first and second verification stations located within the treatment room at spaced locations on opposite sides of the radiation source.

23. A treatment verification method for use with a radiation therapy system including a radiation treatment device for providing radiation treatment, the method comprising:

a) providing automated and manual set up options for setting of treatment field values for the radiation treatment device wherein, in the automated option, treatment field values are automatically entered as received from a computer at a verification station and wherein, in the manual option, the treatment field values are entered by a technologist at a radiation treatment device workstation;

b) setting different predetermined tolerances based on whether the treatment field values are to be entered in an automated manner by the computer in accordance with said automated option or are to be entered manually by the technologist in accordance with said manual option;

c) selecting between said options and proceeding with the selected option;

d) comparing each data entry for the entered treatment field values with a corresponding stored data point of stored treatment field values; and e) using the verification monitor to output an identifier for each data entry which, based on said comparison, is outside of the predetermined tolerances for the option selected.

24. A method of verification of an identification of a patient undergoing treatment administered by a medical treatment practitioner in a treatment room, said method comprising:

providing an identifying card for the patient including a patient identifier capable of being read by a reader device located within the treatment room;

causing the identifying card to be read by said reader device in the treatment room;

generating a characteristic audio signal, previously assigned to the patient and known to the patient, in response to the reading of said identifying card when there is a match between the patient identified and a stored identifier for the patient; and at least temporarily withholding treatment of the patient if any audio signal generated in response to reading of the identifying card by the reader device is not the characteristic audio signal assigned to the patient.

25. A method as claimed in claim 24 wherein the audio signal is also known to the medical practitioner and treatment of the patient is at least temporarily withheld if the patient and the medical practitioner do not agree that any audio signal generated is the characteristic audio signal assigned to the patient.

26. A method according to claim 25 wherein said identifying card includes a photograph of the patient and the photograph is used by the medical practitioner in identifying the patient.

27. A method according to claim 24 wherein said identification card is a part of a treatment file containing treatment data for use by the medical practitioner during treatment, and the card is caused to be read by the medical practitioner to thereby ensure that the medical practitioner takes the treatment file into the treatment room.

28. A method according to claim 27 further comprising generating an electronic record comprising treatment data associated with the treatment to be administered and including said patient identifier, causing the patient identifier of the electronic record to be read by a further reader device in the treatment room, generating said characteristic audio signal in response to reading of said patient identifier of the electronic record, and at least temporarily withholding treatment if any audio signal generated in response to said reading of the patient identifier of the electronic record is not the characteristic audio signal assigned to the patient.

29. A method according to claim 28 wherein said reader devices are caused to read the respective patient identifiers of the card and the electronic record at closely spaced times.

30. A method according to claim 29 wherein the respective patient identifiers are caused to be read by different medical practitioners.

31. A method according to claim 30 wherein the reader devices are located on opposite walls of the treatment room.

32. A method according to claim 24 wherein the reader device and a further reader device are provided as parts of respective verification stations located at spaced locations inside of the treatment room and the stored identifying code is stored at a verification workstation located outside of the treatment room and linked to said respective verification stations.

33. A method according to claim 24 wherein said reader device is part of a first verification station located inside of the treatment room and the stored identifying code is stored at a verification workstation located outside of the treatment room and linked to the first verification station.

34. A method according to claim 33 wherein the identifying card includes a photograph of the patient and the photograph is used by the medical practitioner at the verification workstation in storing the stored identifying code.

35. A system according to claim 22 wherein the optical reader of each of said first and second verification stations comprises a barcode reader.

36. A system according to claim 21 wherein said radiation source comprises an accelerator, said system includes an acceleration workstation including a monitor and said verification workstation is also linked to said accelerator workstation.

37. A system according to claim 21 wherein said verification workstation includes a barcode reader and a card swipe reader.

* * * * *